United States Patent [19]

Suzuki et al.

[11] Patent Number: 4,534,892
[45] Date of Patent: Aug. 13, 1985

[54] FOAMING LIQUID DETERGENT COMPOSITION HAVING A STABLY DISPERSED WATER-INSOLUBLE FINE POWDER

[75] Inventors: Toshio Suzuki, Ichikawa; Hiroshi Watanabe, Funabashi; Rikio Tsushima, Wakayama, all of Japan

[73] Assignee: Kao Corporation, Tokyo, Japan

[21] Appl. No.: 515,654

[22] Filed: Jul. 20, 1983

[30] Foreign Application Priority Data

Jul. 27, 1982 [JP] Japan ................................ 57-130730

[51] Int. Cl.³ ........................ C11D 3/14; C11D 3/30
[52] U.S. Cl. .................................... 252/545; 252/106; 252/155; 252/173; 252/174.23; 252/174.24; 252/544; 252/546; 252/547; 252/548; 252/DIG. 2; 252/DIG. 13; 252/DIG. 14
[58] Field of Search .............. 252/140, 106, 155, 163, 252/173, 174.23, 174.24, 174.25, 523, 526, 528, 531, 532, 535, 536, 539, 541, 545, 546, 547, 550, 551, 554, 555, 558, 544, DIG. 2, DIG. 13, DIG. 14

[56] References Cited

U.S. PATENT DOCUMENTS

| | | | |
|---|---|---|---|
| 3,723,325 | 3/1973 | Parran | 252/106 |
| 3,956,158 | 5/1976 | Donaldson | 252/102 |
| 4,284,533 | 8/1981 | Inamura et al. | 252/542 |
| 4,394,179 | 7/1983 | Ellis et al. | 137/7 |
| 4,396,525 | 8/1983 | Rubin et al. | 252/174.25 |
| 4,417,992 | 11/1983 | Bhattacharyya et al. | 252/88 |
| 4,438,016 | 3/1984 | Kiewert et al. | 252/174.25 |
| 4,454,060 | 6/1984 | Lai et al. | 252/547 |

FOREIGN PATENT DOCUMENTS

| | | |
|---|---|---|
| 3044754 | 6/1981 | Fed. Rep. of Germany . |
| 49117 | 12/1974 | Japan . |
| 48335 | 3/1982 | Japan . |
| 1308190 | 2/1973 | United Kingdom . |
| 2088209 | 6/1982 | United Kingdom . |

*Primary Examiner*—Prince E. Willis
*Attorney, Agent, or Firm*—Oblon, Fisher, Spivak, McClelland & Maier

[57] ABSTRACT

A liquid detergent composition containing an anionic surface active agent and a water-insoluble fine powder, characterized by containing therein a cross linking type amphoteric polymer and an inorganic salt.

Detergents according to the invention are widely applicable to various purposes such as for shampoo, liquid cleanser, etc.

16 Claims, 1 Drawing Figure

FIGURE
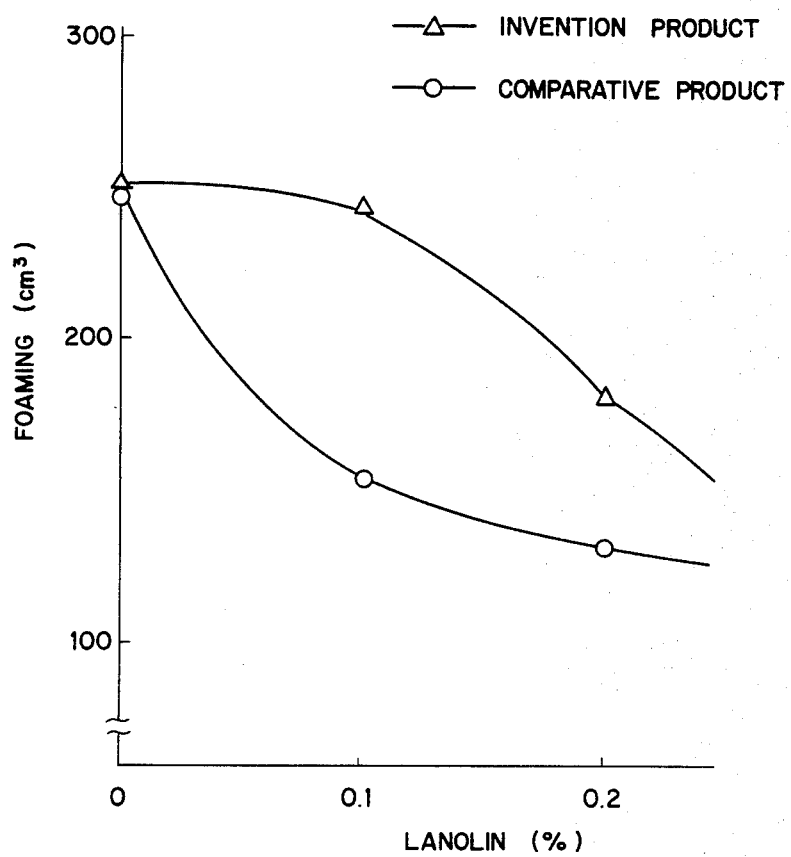

FOAMING LIQUID DETERGENT COMPOSITION HAVING A STABLY DISPERSED WATER-INSOLUBLE FINE POWDER

BACKGROUND OF THE INVENTION (i) Field of the Invention

This invention relates to a liquid detergent composition. More particularly, the invention relates to liquid detergent compositions containing anionic surface active agents and water-insoluble fine powder, in which said water-insoluble fine powder has stably been dispersed, said composition being characterized by containing therein cross linking type amphoteric polymers and inorganic salts.

(ii) Description of the Prior Art

Heretofore it has often been practiced that water-insoluble fine powder is dispersed in liquid detergent compositions in order to impart a pearlescent appearance to the compositions or to enhance the commercial value of the compositions by mixing said compositions with special medicinal agents, sterilizers, suspending agents, etc.

The followings are indispensable requisites to stable dispersion of water-insoluble fine powder in liquid detergent compositions.

(1) The dispersed fine powder should not be coagulated, and (2) the dispersion system should have a high yield value.

Examples of the systems which meet the above requisites include a system having extremely high viscosity and a thixotropic system showing non-Newtonian flow. However, when the former system is applied to prepare liquid detergents, the resulting detergents have such drawbacks that they are difficult to use because they have poor fluidity and, particularly in winter, they don't flow out of the containers. Under such circumstances, various researches have been prosecuted on processes for obtaining liquid systems of non-Newtonian flow, and as a typical prior art in this field, Japanese Patent Publication No. 49117/1974 may be cited.

The publication discloses that water-insoluble fine powder can stably be dispersed in a compound system comprising an anionic surface active agent, an organic group-substituted amine salt and a water-soluble polyacrylic acid when said system is adjusted to pH 6–8 with ammonia, ethanolamine, etc. However, the liquid detergent composition according to the above-mentioned compound system was found to be still disadvantageous in properties such as foamability, by reason that triethanolamine or the like is used as a counter ion to the anionic surface active agent. With the view of improving the detergent foaming property of this detergent composition, a part of water-soluble polyacrylic acid counter ion was replaced with sodium, whereupon the yield value of said liquid detergent composition became almost zero, with the result that the water-insoluble fine powder separated from the system and no satble dispersion system of the water-insoluble fine powder was obtained.

Accordingly, the fact was that no desired liquid detergent compositions were obtained hitherto, said compositions comprising alkali metal salts or the like of anionic surfactants as active detergent ingredients and dispersing stably therein water-insoluble fine powder.

SUMMARY OF THE INVENTION

The present inventors have proceuted extensive studies with the view of obtaining liquid detergent compositions in which water-insoluble fine powder is stably dispersed and no deterioration in detergent foaming property which is inherently essential to detergent is brought about, and as a result, found that the liquid detergent compositions which meet the above-mentioned demand can be obtained by using a specific amphoteric polymer in combination with an inorganic salt in said compositions.

That is, the present invention is to provide a liquid detergent composition containing an anionic surfactant and a water-insoluble fine powder, characterized in that said composition contains therein a cross linking amphoteric polymer and an inorganic salt.

BRIEF DESCRIPTION OF THE DRAWINGS

The sole FIGURE is a graph showing the results of foaming test on the invention product and the comparative product.

DETAILED DESCRIPTION OF THE INVENTION AND PREFERRED EMBODIMENTS

Cross linking type amphoteric polymers used in the present invention are those which are obtained by copolymerization of acidic and basic monomers, or polymerization of amphoteric monomers in the presence of cross liking monomers, and these cross linking type amphoteric polymers are prepared, for example, by processes disclosed in Japanese Patent Application Nos. 112570/1981 and 112575/1981. Representatives of the cross linking type amphoteric polymers are exemplified in the following.

(1) Copolymerization product obtained by polymerizing acidic and basic monomers in the presence of cross linking monomer:

As typical of the title copolymerization product, there may be mentioned a cross linking amphoteric copolymer which is obtained by copolymerizing a monomer mixture comprising 20–80 mol% of an acidic vinyl monomer or its salt, 20–80 mol% of a basic vinyl monomer or its salt and 0.01–5 mol% of a cross linking monomer, at a temperature ranging from 20° to 120° C. in the presence of a radical polymerization initiator.

As used herein, the term acidic vinyl monomer is intended to mean compounds having in a molecule, acid groups such as carboxyl group and sulfonic acid group, and polymerizable vinyl groups. Said compounds include, for example, acrylic acid, methacrylic acid, itaconic acid, maleic anhydride, 2-acrylamide-2-methylpropanesulfonic acid, styrenesulfonic acid, vinylsulfonic acid, allylsulfonic acid, methallylsulfonic acid, etc. Salts of these monomers include sodium salts, potassium salts, ammonium salts, etc. By basic vinyl monomer is meant compounds having in a molecule basic groups such as primary amino, secondary amino or tertiary amino group or the like, and polymerizable vinyl groups. These compounds include, for example, dimethylaminoethyl methacrylate, diethylaminoethyl methacrylate, dimethylaminoethyl methacrylate, diethylaminoethyl acrylate, dimethylaminopropyl methacrylamide, dimethylaminopropyl acrylamide, 2-vinylpyridine, 4-vinylpyridine, dimethylallylamine, diallylmethylamine, etc. Salts of these basic monomers, i.e. quaternary compounds, are intended to include hydrides, methylation products, ethylation products, etc. which have chlorine ion, bromine ion, hydroxyl ion, methylsulfuric acid group, etc. as a counter anion.

A molar proportion of the acidic vinyl monomer to the basic vinyl monomer is 20/80–80/20, preferably 35/65–65/35, more preferably 45/55–55/45. If the mixing proportion is beyond the range of 20/80–80/20, the resulting cross linking copolymer is not sufficiently compatible with water and the object of the present invention is difficult to be attained.

By the term cross linking monomer as used herein is intended to include compounds having in a molecule two or more functional groups capable of reacting with vinyl group, acid or base, and these compounds include, for example, methylenebisacrylamide, methylenebismethacrylamide, butanedioldiacrylate, butanedioldimethacrylate, ethylene glycol diacrylate, ethylene glycol dimethacrylate, polyethylene glycol diacrylate, polyethylene glycol dimethylacrylate, polypropylene glycol diacrylate, polypropylene glycol dimethacrylate, trimethylolpropane triacrylate, trimethylolpropane trimethacrylate, allyl acrylate, allyl methacrylate, glycidyl acrylate, glycidyl methacrylate, 2-hydroxyethyl acrylate, 2-hydroxy methacrylate, diacryloxyethyl phosphate, dimethacryloxyethyl phosphate, triallyl cynaurate, triallyl isocyanurate, divinylbenzene, maleic acid diallylester, polyallyl saccharose, etc. The amount of the cross linking monomer used is 0.01–5 mol%, preferably 0.05–1 mol% based on the total amount of monomers used.

If the amount of this cross linking monomer used is excessively small, the resulting copolymer does not have sufficiently satisfactory dispersing ability and, if said amount is excessively large, the resulting copolymer does not dissolve or swell in water, and thus both cases are undesirable for attaining the object of the present invention.

The copolymerization reaction may be carried out by such conventional procedures, for example, as block polymerization, aqueous solution polymerization, reverse phase suspension polymerization or precipitation polymerization, and the reaction smoothly proceeds in the presence of radical polymerization initiators at a temperature of 20°–120°, preferably 35°–80° C.

Usable radical polymerization initiators are sodium persulfate, potassium persulfate, ammonium persulfate, benzoyl peroxide, hydrogen peroxide, sodium peracetate, cumene hydroperacid and azobisisobutyl nitrile. The amount of radical polymerization initiator, though it may vary depending on the kind of the initiator used, is favorably about 0.01–5% by weight based on the total monomers.

In the practice of the present invention, there may be used other vinyl monomers as optional third components which are copolymerizable with the aforesaid acidic and basic vinyl monomers, though the amount of such other vinyl monomers should be less than 60 mol% based on the total monomers. Usable as the other vinyl monomers referred to above are monovinyl compounds which are polymerizable in the presence of radical polymerization initiators, and the monovinyl compounds include, for example, acrylic acid esters such as methyl acrylate, ethyl acrylate, etc., methacrylic acid esters such as methyl methacrylate, ethyl methacrylate, etc., styrene compounds such as styrene, α-methylstyrene, etc., acrylamide, methacrylamide, vinyl ether, vinyl acetate, etc.

(2) Polymerization product obtained by polymerizing an amphoteric monomer in the presence of a cross linking monomer:

As typical of the captioned polymerization product, there may be mentioned a cross linking type amphoteric polymer which is obtained by polymerizing, in the presence of a radical polymerization initiator at a temperature ranging from 20° C. to 120° C., a monomer mixture comprising 95–99.99 mol% of an amphoteric monomer represented by the undermentioned general formula (I) and 0.01–5 mol% of a cross linking monomer.

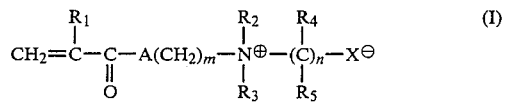

wherein $R_1$, $R_4$ and $R_5$ are individually hydrogen or methyl, $R_2$ and $R_3$ are individually methyl or ethyl, A is —O— or —NH—, X is —$CO_2$, —$SO_3$ or —$PHO_3$, and m and n are individually an integer of 1 to 3.

The amphoteric monomer represented by the general formula (I) can be prepared by reaction of aminoalkyl ester or aminoalkylamide of acrylic acid or methacrylic acid with lactone, sultone or cyclicphosphite.

Usable amphoteric monomers of the general formula (I) include, for example, 3-dimethyl(acryloxyethyl)ammonium.ethanecarboxylate, 3-diethyl(acryloxyethyl)ammonium.ethanecarboxylate, 3-dimethyl(methacryloxyethyl)ammonium.ethanecarboxylate, 3-diethyl(methacryloxyethyl)ammonium.ethanecarboxylate, 3-dimethyl(acryloxyethyl)ammonium.propanesulfonate, 3-diethyl(acryloxyethyl)ammonium.propanesulfonate, 3-dimethyl(methacryloxyethyl)ammonium.propanesulfonate, 3-diethyl(methacryloxyethyl)ammonium.propanesulfonate, 3-dimethyl(acryloxyethyl)ammonium.ethanephosphite, 3-dimethyl(methacryloxyethyl)ammonium.ethanephosphite, 3-dimethyl(acryloxyethyl)ammonium.2-dimethylpropanephosphite, 3-dimethyl(methacryloxyethyl)ammonium.2-dimethylpropanephosphite, etc.

Usable cross linking monomers in this case are the same as mentioned in the foregoing (1).

The molar proportion of the amphoteric monomer to the cross linking monomer used in the polymerization reaction is 99.99/0.01–95/5, preferably 99.95/0.05–99/1.

If the amount of the cross linking monomer used is excessively small, the resulting cross linking type amphoteric polymer does not have sufficient dispersing effect and, inversely if the amount of the cross linking monomer used is excessively large, the resulting cross linking type amphoteric polymer does not dissolve or swell in water, and thus both cases are unsuitable for attaining the object of the present invention.

The polymerization reaction may be effected by any conventional procedure, for example, block polymerization, aqueous solution polymerization, reverse phase suspension polymerization and precipitation polymerization, and the reaction smoothly proceeds in the presence of radical polymerization initiators at a temperature ranging from 20°–120°, preferably 35°–80° C.

Usable radical polymerization initiators are sodium persulfate, potassium persulfate, ammonium persulfate, benzoyl persulfate, hydrogen peroxide, sodium peracetate, cumene hydroperacid, azobisisobutyl nitrile, etc. Generally, the amount of radical polymerization initiator used is desirably about 0.01-5% by weight based on the total monomers. Needless to say, parts of the amphoteric monomer of the general formula (I) may be substituted with other vinyl monomer copolymerizable with said amphoteric monomer and thereby to effect copolymerization. in that case, however, the vinyl monomer used as a substitute therefor should be less than 50 mol%, preferably 30 mol% based on the total monomers. If the proportion of this vinyl monomer is excessively large, the resulting cross linking type amphoteric polymer does not have sufficient dispersing stability in water. These vinyl monomers are monovinyl compounds polymerizable in the presence of radical polymerization initiators, and the compounds include, for example, acrylic acid esters such as methyl acrylate, ethyl acrylate, etc., methacrylic acid esters such as methyl methacrylate, ethyl methacrylate, etc., styrene compounds such as styrene, α-methyl styrene, etc., acrylamide, methacrylamide, vinyl ether, vinyl acetate, etc.

Preferred cross linking type amphoteric polymers of the kind are those having a viscosity (25° C.) in 2 wt% solution (1 mole saline solution) falling within the range of from 500 to 10000 cp.

Inorganic salts used in the present invention are alkali metals, alkaline earth metals or aluminum salts of hydrochloric acid, sulfuric acid, nitric acid, etc. Of such inorganic salts, preferred are potassium sulfate, sodium sulfate, magnesium sulfate, aluminium sulfate, potassium nitrate, sodium nitrate, magnesium nitrate, calcium nitrate, aluminium nitrate, potassium chloride, sodium chloride, magnesium chloride, calcium chloride, aluminium chloride, potassium carbonate, sodium carbonate, and aluminium carbonate, and particularly sodium sulfate, potassium nitrate, sodium nitrate, potassium chloride and sodium chloride are preferable.

With respect to the amount of the inorganic salt to be incorporated into the liquid detergent composition of the present invention, the ratio (weight ratio) of the inorganic salt relative to the cross linking type amphoteric polymer is important, and the amount of the inorganic salt should be 10 to 1/10 times that of the cross linking type amphoteric polymer.

The liquid detergent composition of the present invention is prepared by incorporating the above-mentioned two ingredients in the usual way into a detergent composition containing an anionic surface active agent and a water-insoluble fine powder.

Preferable anionic surfactants are those exemplified below, though any anionic surfactants are usable without particular limitation.

(1) Straight or branched chain alkylbenzenesulfonates having alkyl groups with the average carbon number of 10-16.
(2) Alkyl- or alkenylethoxy sulfates having straight or branched chain alkyl or alkenyl groups with the average carbon number of 8-20 and having added ethylene oxide of 0.5-8 moles on average to the molecule.
(3) Alkyl- or alkenylsulfuric esters having alkyl or alkenyl groups with the average carbon number of 10 to 20.
(4) Olefinsulfonates having in a molecule of 10 to 20 carbon atoms on average.
(5) Alkanesulfonates having in a molecule 10 to 20 carbon atoms on average.
(6) Saturate or unsaturate fatty acid salts having in a molecule 10 to 20 carbon atoms on average.
(7) Alkyl- or alkenylethoxycarboxylates having alkyl or alkenyl groups of the average carbon number of 10 to 20 and having added the average 0.5-8 moles of ethylene oxide to the molecule.
(8) α-sulfofatty acid salts or esters represented by the following formula;

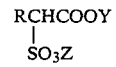

wherein Y is an alkyl group having 1-3 carbon atoms or a counter ion to the anionic surface active agent, Z is a counter ion to the anionic surface active agent, and R is an alkyl or alkenyl group having 10-20 carbon atoms.

(9) Succinic acid derivatives represented by the following formula;

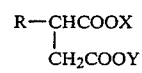

wherein R represents an alkyl or alkenyl group having 6-20 carbon atoms, and X and Y individually represent a counter ion.

Usable as counter ions to the anionic surface active agent are alkali metal ions such as sodium, potassium, etc.; alkaline earth metal ions such as calcium, magnesium, etc.; basic amino acid ions such as ammonium ion, lysine, arginine, etc.; and alkanolamines such as monoethanolamine, diethanolamine, triethanolamine and triisopanolamine, each having 1-3 alkanol groups of 2 or 3 carbon atoms, and particularly sodium ion and ammonium ion are preferred. Of the above-mentioned anionic surface active agents, more preferable are alkyl- or alkenyl sulfates; alkyl- or alkenylethoxysulfates; alkyl- or alkenylethoxycarboxylates; straight or branched chain alkylbenzene-sulfonates and particularly preferable are anionic surface active agents having in a molecule an alkyl chain of the average 12-16 carbon atoms.

Although water-insoluble fine powder used in the present invention is not particularly limited to specific ones, preferably usable are pigments such as silicon dioxide, aluminium oxide, magnesium oxide, titanium oxide, aluminosilicate, silicon carbide, calcium carbonate, calcium phosphate, chromium oxide, barium carbonate, Hansa Yellow, talc, etc.; pearling agents or clouding agents such as mica, fish scale, etc.; such germicidal preservatives as zinc-2-pyridyl-thio-1,1'-dioxide; and abrasives of such natural pulverized products as corundum, emery, silica, quartz sand, doromite, sand, shell, etc. The fine powder usually has a particle size of less than 150μ, preferably less than 50μ, though the particle size varies depending on the purpose for which the powder is used, and a particularly preferable particle size is 15-40μ in the case of liquid cleanser and 0.1-5μ in the case of detergent for body application.

The proportions of the ingredients used in the liquid detergent of the present invention are as in the following.

|  | Mixing range (wt %) | Particularly preferred range (wt %) |
|---|---|---|
| Anionic surfactant | 5-30 | 10-25 |
| Water-insoluble fine powder | 0.1-15 | 0.5-3 |
| Cross linking type amphoteric polymer | 0.1-5 | 0.4-0.8 |

|  | Mixing range (wt %) | Particularly preferred range (wt %) |
|---|---|---|
| Inorganic salt | 1–10 | 2–6 |

In addition to the above-mentioned ingredients and water as medium, the detergent composition of the present invention can be incorporated, according to the object and use thereof, with optional components known per se to such an extent that they do not impede the effect of the present invention.

For example, nonionic surface active agents, amphoteric surface active agents and cationic surface active agents may be used in combination with the anionic surface active agents. Other components which may be incorporated are dissolving agents such as propylene glycol, glycerin, urea, etc.; viscosity regulators such as ethanol, isopropanol, higher alcohol, hydroxyethyl cellulose, hydroxypropyl cellulose, etc.; perfumes, dyes, ultraviolet absorbers, antioxidants, water-soluble anti-dandruff agents, sterilizers, preservatives, etc.

The liquid detergent composition of the present invention obtained in the aforementioned manner is applicable to various purposes such as for shampoo, liquid cleanser, detergent for tableware and kitchenware, detergent for residential purposes, detergent for wool and silk, body shampoo, detergent for fine fabric, etc.

The present invention will now be further explained by way of illustration with reference to referential synthesis examples and other examples, which should not be construed as limiting the invention.

REFERENTIAL SYNTHESIS EXAMPLE 1

Cross linking type amphoteric polymer (AA/QDM; molar ratio 1:1):

To a 500 ml separable flask equipped with a stirrer, thermometer, reflux condenser and a dropping funnel were fed 120 g of water, 34.4 g of 2-methacryloxyethyl dimethylammonium ethosulfate (QDM), 12.8 g of acrylic acid (AA), 1.26 g of methylenebisacrylamide as a cross linking agent, 0.15 g of potassium persulfate and 0.06 g of sodium laurylsulfate. The flask was then immersed in a thermostat kept at 40° C., to effect polymerization for 6 hours while shaking from time to time. The polymerization system which gelled in its entirety was poured into about 2 liters of caustic soda, allowed to stand overnight, and desalted in an ion exchange water to obtain the captioned cross linking type amphoteric polymer.

REFERENTIAL SYNTHESIS EXAMPLE 2

Cross linking type amophoteric polymer (AMPS/QDM; molar ratio 1:1):

To a 500 ml separable flask equipped with a stirrer, thermometer, reflux condenser and a dropping funnel was fed 230 ml of hexane containing 1.8% by weight of Span 60 and heated at 60° C. to dissolve. Subsequently, to the flask was fed 50 g of water, 17.18 g of 2-acrylamine-2-methylpropanesulfonic acid (AMPS), 13.05 g of 2-methacryloxyethyl diethylammonium ethosulfate (QDM), 1.26 g of methylene-bis-acrylamide as a cross linking agent, and 0.1 g of potassium persulfate. Polymerization was effected for 3 hours at a temperature elevated to 65° C. After cooling, the polymerization product was decanted to remove the hexane therefrom, deaerated to 200 mmHg at 70° C. and then dried. The thus dried polymerization product was washed three times with an organic solvent, isopropanol, to remove the Span 60 therefrom to obtain the captioned cross linking type amphoteric polymer.

REFERENTIAL SYNTHESIS EXAMPLE 3

Cross linking type amophoteric polymer (carbobetaine:

(a) Synthesis of amphoteric monomer

To a 1 liter separable flask equipped with a stirrer, thermometer, reflux condenser and a dropping funnel, were fed 314 g (2.0 moles) of dimethylaminoethyl methacrylate (DMAEMA) and 200 g of acetone, followed by cooling to 0° C. Subsequently, to the flask was added drop-wise a solution of 144 g (2.0 moles) of β-propiolactone disolved in 100 g of acetone over a period of 1 hour, and the resulting mixture was stirred for 4 hours at 0° C. and allowed to stand overnight. The mixture was separated and purified to obtain the captioned amphoteric monomer.

(b) Synthesis of amphoteric monomer

To a 100 ml glass ampul were fed 22.9 g (0.1 mol) of carbobetaine monomer obtained in (a), 50 g of water, 0.03 g (0.2 mol) of a cross linking agent, methylene-bis-acrylamide, and 0.1 g of potassium persulfate, and the ampul was sealed. The sealed ampul was immersed in a thermostat kept at 70° C., and shaked for 7 hours to effect polymerization for 7 hours. The polymerization system which gelled in its entirety was poured into about 1 liter of alcohol to obtain the captioned cross linking type amphoteric polymer.

REFERENTIAL SYNTHESIS EXAMPLE 4

Cross linking type amphoteric polymer (MAA/DMAEMA; molar ratio 1:1):

Using a 14.8 g of methacrylic acid (MAA) and 24.2 g of dimethylaminoethyl methacrylate (DMAEMA), the reaction was carried out in the manner similar to that in Referential Synthesis Example 1 to obtain the captioned cross linking type amphoteric polymer.

REFERENTIAL SYNTHESIS EXAMPLE 5

Cross linking type amphoteric polymer (AMPS/QDM; molar ratio 1:1):

Using 20.7 g of 2-acrylamide-2-methylpropanesulfonic acid (AMPS) and 17.1 g of methacryloxyethyl trimethylammonium (QDM), the reaction was carried out in the manner similar to that in Referential Synthesis Example 2 to obtain the captioned cross linking type amphoteric polymer.

EXAMPLE 1

A shampoo of the following composition was prepared, and was examined for its viscosity and storage stability. The results obtained are shown in Table 1.

Composition

| Anionic surface active agent (Table 1) | 18.0% |
|---|---|
| Lauric acid diethanolamide | 3.0 |
| Cross linking type amphoteric polymer (the polymer obtained in Referential Synthesis Example 1) | (Table 1) |
| Sodium chloride | (Table 1) |
| Zinc-2-pyridyl-thio-1,1'-dioxide (particle size 2 μ) | 1.0 |
| Benzoic acid | 0.15 |

-continued

| Perfume | 0.1 |
|---|---|
| Coloring matter | 0.005 |
| Water | Balance |

Test method

Viscosity

The composition was placed in a viscobeaker kept at a predetermined temperature and was measured its viscosity by means of B type viscometer (Rotor No. 3, revolution: 12 rpm).

Storage stability

The composition was placed in a 100 cc glass bottle and was sealed and stored at various temperatures. Stability was observed after a three-month storage.
O . . . No separation was observed (stable).
X . . . Separation was observed.

Results

TABLE 1

| | Anionic surface active agent | Amount of cross linking type amphoteric polymer (%) | Amount of sodium chloride (%) | Viscosity (cp) at 30° C. | Storage stability (3 months) | | |
|---|---|---|---|---|---|---|---|
| | | | | | 50° C. | 40° C. | −10° C. |
| Invention Product 1 | Ammonium laurylsulfate | 0.4 | 3.0 | 1300 | O | O | O |
| Invention Product 2 | Sodium laurylsulfate | 0.4 | 3.0 | 1000 | O | O | O |
| Comparative Product 1 | Ammonium laurylsulfate | — | 3.0 | 100 | X | X | X |
| Comparative Product 2 | Laurylsulfuric acid triethanolamine | — | — | 550 | X | X | X |

EXAMPLE 2

A shampoo of the following composition was prepared and examined in the manner similar to that in Example 1 for its viscosity and storage stability to obtain the results as shown in Table 2.

Composition

| Sodium polyoxyethylene (E = 2.5) laurel ether sulfate | 18.0% |
|---|---|
| Cross linking type amphoteric polymer (the polymer obtained in Referential Synthetic Example 1) | 0.4 |
| Sodium chloride | (Table 2) |
| Zinc-2-pyridyl-thio-1,1′-dioxide (particle size 2 μ) | 1.0 |
| Benzoic acid | 0.15 |
| Perfume | 0.1 |
| Coloring matter | 0.005 |
| Water | Balance |

Results

TABLE 2

| | Amount of sodium Chloride (%) | Viscosity (cp) 30° C. | Storage stability (3 months) | | |
|---|---|---|---|---|---|
| | | | 50° C. | 40° C. | −10° C. |
| Invention Product | 3.0 | 860 | O | O | O |
| Comparative Product | — | less than 50 | X | X | X |

EXAMPLE 3

A detergent for fine fabric of the following composition was prepared and examined for its viscosity and storage stability in the manner similar to that in Example 1 to obtain the results as shown in Table 3.

Composition

| Polyoxyethylene (E = 2.5) lauryl ether sodium sulfate | 18.0% |
|---|---|
| Cross linking type amphoteric polymer (the polymer obtained in Referential Synthetic Example 2) | 0.6 |
| Sodium chloride | (Table 3) |
| Titanium oxide (particle size 5 μ) | 1.0 |
| Benzoic acid | 0.15 |
| Perfume | 0.1 |
| coloring matter | 0.05 |
| Water | Balance |

Results

TABLE 3

| | Amount of sodium chloride (%) | Viscosity (cp) 30° C. | Storage stability (3 months) | | |
|---|---|---|---|---|---|
| | | | 50° C. | 40° C. | −10° C. |
| Invention Product | 3 | 2000 | O | O | O |
| Comparative Product | — | less than 50 | X | X | X |

EXAMPLE 4

A shampoo was prepared by mixing the following components in the usual way.

Composition

| 1 | Polyoxyethylene (E = 2.5) lauryl ether sodium sulfate | 18.0% |
|---|---|---|
| 2 | Cross linking type amphoteric polymer (the polymer obtained in Referential Synthetic Example 1) | 0.4 |

-continued

| | | |
|---|---|---|
| 3 | Sodium chloride | 3.0 |
| 4 | Pearling agent (fish scale; particle size 30 μ) | 1.0% |
| 5 | Benzoic acid | 0.15 |
| 6 | Perfume | 0.1 |
| 7 | Coloring matter | 0.05 |
| 8 | Water | Balance |

The shampoo composition thus obtained had a viscosity of 900 cp at 30° C., and excellent storage stability at the aforementioned temperatures as varied.

EXAMPLE 5

A liquid cleanser was prepared by mixing the following components in the usual way.

Composition

| | | |
|---|---|---|
| 1 | Polyoxyethylene (E = 2.5) lauryl ether sodium sulfate | 18.0% |
| 2 | Cross linking amphoteric polymer (the polymer obtained in Referential Synthesis Example 1) | 0.6 |
| 3 | Sodium chloride | 3.0 |
| 4 | Silicon dioxide (average particle size 30 μ) | 1.0 |
| 5 | Benzoic acid | 0.15 |
| 6 | Perfume | 0.1 |
| 7 | Coloring matter | 0.05 |
| 8 | Water | Balance |

The liquid cleanser composition thus obtained had a viscosity of 2500 cp at 30° C. and excellent storage stability at the aforementioned temperatures as varied.

EXAMPLE 6

The invention product 1 obtained in Example 1 and the comparative product 2 were compared in foaming power to obtain the results as shown in the accompanying FIG. 1.

Conditions under which the foaming force test was conducted

A 1% solution of detergent composition kept at 40° C., to which 0.1 or 0.2% of lanolin had been added, was stirred for 5 minutes at 1000 rpm by using an inversion stirrer, followed by standing for 30 seconds, and a cubic volume of the foam formed at that time was measured for judging the foaming power.

EXAMPLE 7

A shampoo of the following composition was prepared and examined for storage stability in the manner similar to that in Example 1 to obtain the results as shown in Table 4.

Composition

| | |
|---|---|
| Polyoxyethylene (E = 2.5) lauryl ether sodium sulfate | 18.0% |
| Cross linking type amphoteric polymer | (Table 4) |
| Inorganic salt | (Table 4) |
| Zinc-2-pyridyl-thio-1,1′-dioxide (particle size 2 μ) | 1.0 |
| Benzoic acid | 0.15 |
| Perfume | 0.1 |
| Coloring matter | 0.005 |
| Water | Balance |

TABLE 4

| | Cross linking type amphoteric polymer [Amount mixed (%)] | Inorgania salt [Amount mixed (%)] | Storage stability (3 months) | | |
|---|---|---|---|---|---|
| | | | 50° C. | 40° C. | −10° C. |
| Inventive Product | Polymer obtained in Referential Synthetic | | | | |
| | Example 5 [0.4] | Sodium chloride [2.0] | O | O | O |
| | Example 1 [0.4] | Sodium sulfate [2.0] | O | O | O |
| | Example 3 [0.5] | Lithium chloride [2.1] | O | O | O |
| | Example 4 [0.4] | Potassium chloride [1.8] | O | O | O |
| | Example 1 [0.5] | Calcium chloride [2.0] | O | O | O |
| | Example 5 [0.6] | Aluminium chloride [3.0] | O | O | O |
| | Example 4 [0.5] | Sodium carbonate [1.5] | O | O | O |
| Comparative Product | Example 5 [0.4] | — | X | X | X |
| | Example 3 [0.5] | — | X | X | X |
| | Example 4 [0.4] | — | X | X | X |
| | Example 5 [0.6] | — | X | X | X |
| | Example 4 [0.5] | — | X | X | X |

What is claimed is:

1. A liquid detergent comprising:
   (a) an anionic surface active agent;
   (b) a water-insoluble fine powder selected from the group consisting of silicon dioxide, aluminium oxide, mangesium oxide, titanium oxide, aluminosilicate, silicon carbide, calcium carbonate, calcium phosphate, chromium oxide, barium carbonate, Hansa Yellow, talc, mica, fish scale, zinc-2-pyridyl-thio-1,1′-dioxide, corundum, emery, silica, quartz sand, doromite, sand, shell, and mixtures thereof;
   (c) a cross-linking amphoteric polymer selected from the group consisting of (1) a copolymerization product obtained by polymerizing acidic vinyl and basic vinyl monomers in the presence of a cross-linking monomer, and (2) a polymerization product obtained by polymerizing an amphoteric monomer in the presence of a cross-linking monomer; and,
   (d) an inorganic salt selected from the group consisting of potassium sulfate, sodium sulfate, mangesium sulfate, aluminium sulfate, potassium nitrate, sodium nitrate, magnesium nitrate, calcium nitrate, aluminium nitrate, potassium chloride, sodium chloride, magnesium chloride, calcium chloride, aluminium chloride, potassium carbonate, sodium carbonate, aluminium carbonate, and mixtures thereof;

said liquid detergent being further characterized in that it comprises the anionic surface active agent in a weight percent range of from 5 to 30, the water-insoluble fine powder in a weight percent range of from 0.1 to 15, the cross-linking type amphoteric polymer in a weight percent range of from 0.1 to 5, and the inorganic salt in a weight percent range of from 1 to 10.

2. The liquid detergent of claim 1 wherein said cross-linking amphoteric polymer is obtained by copolymerizing a monomer mixture comprising 20 to 80 mole % of an acidic vinyl monomer or its salt, 20 to 80 mole % of a basic vinyl monomer or its salt, and 0.01 to 5 mole % of a cross-linking monomer.

3. The liquid detergent of claim 2 wherein said monomer mixture is copolymerized at a temperature ranging from 20° C. to 120° C.

4. The liquid detergent of claim 3 wherein said monomer mixture is copolymerized in the presence of a radical polymerization initiator.

5. The liquid detergent of claim 1 wherein said acidic vinyl monomer comprises a carboxyl group or a sulfonic acid group.

6. The liquid detergent of claim 1 wherein said basic vinyl monomer comprises a primary amino group, a secondary amino group, or a tertiary amino group.

7. The liquid detergent of claim 1 wherein said cross-linking monomer comprises at least two functional groups, said functional groups being capable of reacting with a vinyl group, an acid group, or a base group.

8. The liquid detergent of claim 4 wherein said radical polymerization initiator is used in a range of about 0.01 to 5% by weight based on total monomers.

9. The liquid detergent of claim 2 further comprising up to 60 mole % based on total monomers of a vinyl monomer.

10. The liquid detergent of claim 1 wherein said amphoteric monomer is

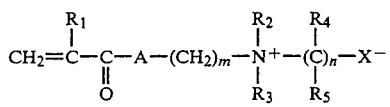

wherein $R_1$, $R_4$ and $R_5$ are each individually hydrogen or methyl; $R_2$ and $R_3$ are each individually methyl or ethyl; A is O or NH; X is $CO_2$, $SO_3$, or $PHO_3$; and m and n are each individually an integer of from 1 to 3.

11. The liquid detergent of claim 10 wherein said amphoteric monomer is polymerized in the presence of from 0.01 to 5 mole % of a cross-linking monomer and wherein said amphoteric monomer is used in an amount of from 99.9 to 95 mole %.

12. The liquid detergent of claim 10 wherein said amphoteric polymer is polymerized at a temperature of from 20° to 120° C.

13. The liquid detergent of claim 1 wherein said cross-linking amphoteric polymer has a viscosity in 2 weight % saline solution, falling within the range of from 500 to 10000 cps as measured at 25° C.

14. The liquid detergent of claim 1 wherein said inorganic salt comprises sodium sulfate, potassium nitrate, sodium nitrate, potassium chloride, sodium chloride, or mixtures thereof.

15. The liquid detergent of claim 1 wherein said inorganic salt is used in a weight ratio relative to the cross-linking amphoteric polymer of from 10:1 to 1:10.

16. The liquid detergent of claim 1 wherein said water-insoluble fine powder has a particle size of up to 150μ.

* * * * *